(12) United States Patent
Dreyfuss et al.

(10) Patent No.: US 8,801,755 B2
(45) Date of Patent: *Aug. 12, 2014

(54) SUTURE ANCHOR (71) Applicant: Arthrex, Inc., Naples, FL (US)

(72) Inventors: Peter J. Dreyfuss, Naples, FL (US); William C. Benavitz, Naples, FL (US)

(73) Assignee: Arthrex, Inc., Naples, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/148,460

(22) Filed: Jan. 6, 2014

(65) Prior Publication Data

US 2014/0121701 A1    May 1, 2014

Related U.S. Application Data (63) Continuation of application No. 13/933,575, filed on Jul. 2, 2013, now Pat. No. 8,623,052, which is a continuation of application No. 12/751,266, filed on Mar. 31, 2010, which is a continuation of application No. 11/097,172, filed on Apr. 4, 2005, now Pat. No. 8,343,186.

(60) Provisional application No. 60/559,425, filed on Apr. 6, 2004.

(51) Int. Cl.
A61B 17/04    (2006.01)

(52) U.S. Cl.
CPC ..... *A61B 17/0401* (2013.01); *A61B 2017/0414* (2013.01); *A61B 2017/044* (2013.01)
USPC ....................................... 606/232

(58) Field of Classification Search
CPC ................. A61B 17/0401; A61B 2017/0414; A61B 2017/044; A61B 2017/0409; A61B 2017/0446; A61B 2017/0448

USPC ........... 606/232, 74, 300, 309, 312; 411/320, 411/142, 199, 216, 356, 357, 76, 350, 555
See application file for complete search history.

(56) References Cited

U.S. PATENT DOCUMENTS

| | | |
|---|---|---|
| 1,610,309 A | 12/1926 | Niederer |
| 1,925,174 A | 9/1933 | Creamean |

(Continued)

FOREIGN PATENT DOCUMENTS

| | | |
|---|---|---|
| CA | 2045903 | 6/1991 |
| EP | 0951869 A1 | 10/1999 |

(Continued)

OTHER PUBLICATIONS

European Search Report for EP Application No. 05102676.3 dated Aug. 29, 2005.

(Continued)

*Primary Examiner* — Dianne Dornbusch
(74) *Attorney, Agent, or Firm* — Carlson, Gaskey & Olds, P.C.

(57) ABSTRACT

A suture anchor assembly includes an anchor having a proximal end, a distal end, a longitudinal axis, a first length, and an internal passage within the anchor. The internal passage begins at an opening in the proximal end and has a second length shorter than the first length. A support structure fixed longitudinally relative to the anchor extends across the internal passage and has a third length shorter than the second length. A suture within the internal passage is received about a distal surface of the support structure. A suture extends out of the opening in the proximal end. A driver includes a cannula having a distal opening and a proximal opening, and the suture is received within the cannula. A first end and the second end of the suture extend outside of the proximal opening, the driver having a drive surface near the distal opening that engages the anchor.

30 Claims, 4 Drawing Sheets

(56) References Cited

U.S. PATENT DOCUMENTS

| | | |
|---|---|---|
| 2,045,903 A | 6/1936 | Fortin |
| 2,121,193 A | 6/1938 | Hanicke |
| 2,329,398 A | 9/1943 | Duffy |
| 2,381,050 A | 8/1945 | Hardinge |
| 2,490,364 A | 2/1948 | Livingston |
| 2,472,103 A | 6/1949 | Giesen |
| 2,562,419 A | 7/1951 | Ferris |
| 2,699,774 A | 1/1955 | Livingston |
| 3,143,916 A | 8/1964 | Rice |
| 3,420,929 A | 1/1969 | Morin |
| 3,768,635 A | 10/1973 | Eggert |
| 3,842,825 A | 10/1974 | Wagner |
| 3,861,269 A | 1/1975 | Laverty |
| 3,910,281 A | 10/1975 | Kletschka et al. |
| 3,951,261 A | 4/1976 | Mandel et al. |
| 3,990,438 A | 11/1976 | Pritchard |
| 4,006,747 A | 2/1977 | Kronenthal et al. |
| 4,013,071 A | 3/1977 | Rosenberg |
| 4,135,623 A | 1/1979 | Thyen |
| 4,175,555 A | 11/1979 | Herbert |
| 4,244,370 A | 1/1981 | Furlow et al. |
| 4,275,717 A | 6/1981 | Bolesky |
| 4,289,124 A | 9/1981 | Zickel |
| 4,301,551 A | 11/1981 | Dore et al. |
| 4,351,069 A | 9/1982 | Ballintyn et al. |
| 4,424,898 A | 1/1984 | Thyen et al. |
| 4,454,875 A | 6/1984 | Pratt et al. |
| 4,467,478 A | 8/1984 | Jurgutis |
| 4,483,023 A | 11/1984 | Hoffman, Jr. et al. |
| 4,507,817 A | 4/1985 | Staffeld |
| 4,519,100 A | 5/1985 | Wills et al. |
| 4,520,511 A | 6/1985 | Gianezio et al. |
| 4,537,185 A | 8/1985 | Stednitz |
| 4,539,981 A | 9/1985 | Tunc |
| 4,590,928 A | 5/1986 | Hunt et al. |
| 4,597,776 A | 7/1986 | Ullman et al. |
| 4,605,414 A | 8/1986 | Czajka |
| 4,632,100 A | 12/1986 | Somers et al. |
| 4,633,869 A | 1/1987 | Schmieding |
| 4,640,271 A | 2/1987 | Lower |
| 4,672,957 A | 6/1987 | Hourahane |
| 4,693,654 A | 9/1987 | Bettini |
| 4,712,542 A | 12/1987 | Daniel et al. |
| 4,723,541 A | 2/1988 | Reese |
| 4,738,255 A | 4/1988 | Goble et al. |
| 4,741,330 A | 5/1988 | Hayhurst |
| 4,750,492 A | 6/1988 | Jacobs |
| 4,756,653 A | 7/1988 | Berger |
| 4,784,126 A | 11/1988 | Hourahane |
| 4,815,467 A | 3/1989 | Chestnut |
| 4,870,957 A | 10/1989 | Goble et al. |
| 4,898,156 A | 2/1990 | Gatturna et al. |
| 4,946,468 A | 8/1990 | Li |
| 4,963,144 A | 10/1990 | Huene |
| 4,976,715 A | 12/1990 | Bays et al. |
| 4,988,351 A | 1/1991 | Paulos et al. |
| 5,002,550 A | 3/1991 | Li |
| 5,002,563 A | 3/1991 | Pyka et al. |
| 5,019,079 A | 5/1991 | Ross |
| 5,037,422 A | 8/1991 | Hayhurst et al. |
| 5,041,129 A | 8/1991 | Hayhurst et al. |
| 5,047,030 A | 9/1991 | Draenert |
| 5,059,201 A | 10/1991 | Asnis |
| 5,061,181 A | 10/1991 | Niznick |
| 5,067,956 A | 11/1991 | Buford, III et al. |
| 5,100,417 A * | 3/1992 | Cerier et al. .................. 606/139 |
| 5,100,471 A | 3/1992 | Winnik et al. |
| 5,102,414 A | 4/1992 | Kirsch |
| 5,102,421 A | 4/1992 | Anspach, Jr. |
| 5,139,499 A | 8/1992 | Small et al. |
| 5,141,520 A | 8/1992 | Goble et al. |
| 5,152,790 A | 10/1992 | Rosenberg et al. |
| 5,156,616 A | 10/1992 | Meadows et al. |
| 5,163,960 A | 11/1992 | Bonutti |
| 5,176,682 A | 1/1993 | Chow |
| 5,180,382 A | 1/1993 | Frigg et al. |
| 5,207,679 A | 5/1993 | Li |
| 5,217,486 A | 6/1993 | Rice et al. |
| 5,224,946 A | 7/1993 | Hayhurst et al. |
| 5,236,445 A | 8/1993 | Hayhurst et al. |
| 5,242,447 A | 9/1993 | Borzone |
| 5,246,441 A | 9/1993 | Ross et al. |
| 5,250,055 A | 10/1993 | Moore et al. |
| 5,258,016 A * | 11/1993 | DiPoto et al. .................. 606/232 |
| 5,261,914 A | 11/1993 | Warren |
| 5,268,001 A | 12/1993 | Nicholson et al. |
| 5,275,176 A | 1/1994 | Chandler |
| 5,285,016 A | 2/1994 | Narizuka et al. |
| 5,306,290 A | 4/1994 | Martins et al. |
| 5,312,438 A | 5/1994 | Johnson |
| 5,320,626 A | 6/1994 | Schmieding |
| 5,327,896 A | 7/1994 | Schmieding |
| 5,330,468 A | 7/1994 | Burkhart |
| 5,336,240 A | 8/1994 | Metzler et al. |
| 5,350,383 A | 9/1994 | Schmieding et al. |
| 5,364,400 A | 11/1994 | Rego, Jr. et al. |
| 5,370,662 A | 12/1994 | Stone et al. |
| 5,375,956 A | 12/1994 | Pennig |
| 5,380,334 A | 1/1995 | Torrie et al. |
| 5,383,905 A | 1/1995 | Golds et al. |
| D357,534 S | 4/1995 | Hayes |
| 5,403,136 A | 4/1995 | Mathys |
| 5,411,506 A | 5/1995 | Goble et al. |
| 5,417,533 A | 5/1995 | Lasner |
| 5,417,691 A | 5/1995 | Hayhurst |
| 5,417,712 A | 5/1995 | Whittaker et al. |
| D359,557 S | 6/1995 | Hayes |
| 5,423,860 A | 6/1995 | Lizardi et al. |
| 5,441,502 A | 8/1995 | Bartlett |
| 5,441,508 A | 8/1995 | Gazielly et al. |
| 5,443,482 A | 8/1995 | Stone et al. |
| 5,447,401 A | 9/1995 | Jones et al. |
| 5,456,685 A | 10/1995 | Huebner |
| 5,462,644 A | 10/1995 | Woodson |
| 5,464,427 A | 11/1995 | Curtis et al. |
| 5,466,243 A | 11/1995 | Schmieding et al. |
| 5,470,334 A | 11/1995 | Ross et al. |
| 5,480,403 A | 1/1996 | Lee et al. |
| 5,492,442 A | 2/1996 | Lasner |
| 5,501,695 A | 3/1996 | Anspach, Jr. et al. |
| 5,501,696 A | 3/1996 | Trott |
| 5,505,736 A | 4/1996 | Reimels et al. |
| 5,520,692 A | 5/1996 | Ferrante |
| 5,522,843 A | 6/1996 | Zang |
| 5,522,844 A | 6/1996 | Johnson |
| 5,534,011 A | 7/1996 | Greene, Jr. et al. |
| 5,545,180 A | 8/1996 | Le et al. |
| 5,549,617 A | 8/1996 | Green et al. |
| 5,556,428 A | 9/1996 | Shah |
| 5,562,664 A | 10/1996 | Durlacher et al. |
| 5,562,672 A | 10/1996 | Huebner et al. |
| 5,562,689 A | 10/1996 | Green et al. |
| 5,569,305 A | 10/1996 | Bonutti |
| 5,569,306 A | 10/1996 | Thal |
| 5,571,139 A | 11/1996 | Jenkins, Jr. |
| 5,573,547 A | 11/1996 | LeVeen et al. |
| 5,573,548 A | 11/1996 | Nazre et al. |
| 5,575,801 A | 11/1996 | Habermeyer et al. |
| 5,575,819 A | 11/1996 | Amis |
| 5,578,057 A | 11/1996 | Wenstrom, Jr. |
| 5,584,835 A | 12/1996 | Greenfield |
| 5,584,839 A | 12/1996 | Gieringer |
| 5,591,207 A | 1/1997 | Coleman |
| 5,593,410 A | 1/1997 | Vrespa |
| 5,593,425 A | 1/1997 | Bonutti et al. |
| 5,601,557 A | 2/1997 | Hayhurst |
| 5,607,432 A | 3/1997 | Fucci |
| 5,618,314 A | 4/1997 | Harwin et al. |
| 5,624,446 A | 4/1997 | Harryman, II |
| 5,626,613 A | 5/1997 | Schmieding |
| 5,634,926 A | 6/1997 | Jobe |
| 5,637,112 A | 6/1997 | Moore et al. |
| 5,643,269 A | 7/1997 | Harle |
| 5,643,273 A | 7/1997 | Clark |

(56) References Cited

U.S. PATENT DOCUMENTS

| | | |
|---|---|---|
| 5,643,320 A | 7/1997 | Lower et al. |
| 5,643,321 A | 7/1997 | McDevitt |
| 5,645,545 A | 7/1997 | Bryant |
| 5,645,547 A | 7/1997 | Coleman |
| 5,645,589 A | 7/1997 | Li |
| 5,647,874 A | 7/1997 | Hayhurst |
| 5,658,313 A | 8/1997 | Thal |
| 5,662,658 A | 9/1997 | Wenstrom, Jr. |
| 5,665,112 A | 9/1997 | Thal |
| 5,667,509 A | 9/1997 | Westin |
| D385,352 S | 10/1997 | Bales et al. |
| 5,681,318 A | 10/1997 | Pennig et al. |
| 5,681,333 A | 10/1997 | Burkhart et al. |
| 5,683,401 A | 11/1997 | Schmieding et al. |
| 5,683,419 A | 11/1997 | Thal |
| 5,685,313 A | 11/1997 | Mayevsky |
| 5,690,649 A | 11/1997 | Li |
| 5,690,676 A | 11/1997 | DiPoto et al. |
| 5,690,677 A | 11/1997 | Schmieding et al. |
| 5,697,950 A | 12/1997 | Fucci et al. |
| 5,702,397 A | 12/1997 | Goble et al. |
| 5,702,398 A | 12/1997 | Tarabishy |
| 5,707,394 A | 1/1998 | Miller et al. |
| 5,709,708 A | 1/1998 | Thal |
| 5,720,765 A | 2/1998 | Thal |
| 5,720,766 A | 2/1998 | Zang et al. |
| 5,725,529 A | 3/1998 | Nicholson et al. |
| 5,725,541 A | 3/1998 | Anspach, III et al. |
| 5,728,136 A | 3/1998 | Thal |
| 5,733,307 A | 3/1998 | Dinsdale |
| 5,738,685 A | 4/1998 | Halm et al. |
| 5,741,300 A | 4/1998 | Li |
| 5,743,914 A | 4/1998 | Skiba |
| 5,749,878 A | 5/1998 | Bracy et al. |
| 5,755,721 A | 5/1998 | Hearn |
| 5,782,864 A | 7/1998 | Lizardi |
| 5,782,865 A | 7/1998 | Grotz |
| 5,792,142 A | 8/1998 | Galitzer |
| 5,797,963 A | 8/1998 | McDevitt |
| 5,810,854 A | 9/1998 | Beach |
| 5,814,051 A * | 9/1998 | Wenstrom, Jr. ............. 606/104 |
| 5,814,071 A | 9/1998 | McDevitt et al. |
| 5,824,011 A | 10/1998 | Stone et al. |
| 5,827,291 A | 10/1998 | Fucci et al. |
| 5,843,087 A | 12/1998 | Jensen et al. |
| 5,843,127 A | 12/1998 | Li |
| 5,851,219 A * | 12/1998 | Goble et al. ............. 606/232 |
| 5,860,978 A | 1/1999 | McDevitt et al. |
| 5,860,983 A | 1/1999 | Wenstrom, Jr. |
| 5,865,559 A | 2/1999 | Yang |
| 5,868,762 A | 2/1999 | Cragg et al. |
| 5,868,789 A * | 2/1999 | Huebner ............. 606/232 |
| 5,879,372 A | 3/1999 | Bartlett |
| 5,885,294 A | 3/1999 | Pedlick et al. |
| 5,891,168 A | 4/1999 | Thal |
| 5,893,850 A | 4/1999 | Cachia |
| 5,902,321 A | 5/1999 | Caspari et al. |
| 5,911,721 A * | 6/1999 | Nicholson et al. ............. 606/326 |
| 5,935,129 A | 8/1999 | McDevitt et al. |
| 5,948,000 A | 9/1999 | Larsen et al. |
| 5,948,001 A | 9/1999 | Larsen |
| 5,951,559 A | 9/1999 | Burkhart |
| 5,957,953 A | 9/1999 | DiPoto et al. |
| 5,964,764 A | 10/1999 | West, Jr. et al. |
| 5,964,783 A | 10/1999 | Grafton et al. |
| 5,968,044 A | 10/1999 | Nicholson et al. |
| 5,980,558 A | 11/1999 | Wiley |
| 5,993,451 A | 11/1999 | Burkhart |
| 5,993,459 A | 11/1999 | Larsen et al. |
| 6,007,567 A | 12/1999 | Bonutti |
| 6,013,083 A | 1/2000 | Bennett |
| 6,022,373 A | 2/2000 | Li |
| 6,024,758 A | 2/2000 | Thal |
| 6,027,523 A | 2/2000 | Schmieding |
| 6,030,162 A | 2/2000 | Huebner |
| 6,036,694 A | 3/2000 | Goble et al. |
| 6,045,573 A | 4/2000 | Wenstrom, Jr. et al. |
| 6,045,574 A | 4/2000 | Thal |
| 6,056,751 A | 5/2000 | Fenton, Jr. |
| 6,086,608 A | 7/2000 | Ek et al. |
| 6,096,041 A | 8/2000 | Gellman et al. |
| 6,117,162 A | 9/2000 | Schmieding et al. |
| 6,129,762 A | 10/2000 | Li |
| 6,143,017 A | 11/2000 | Thal |
| 6,149,669 A | 11/2000 | Li |
| 6,156,039 A | 12/2000 | Thal |
| 6,159,235 A | 12/2000 | Kim |
| 6,200,329 B1 | 3/2001 | Fung et al. |
| 6,214,031 B1 | 4/2001 | Schmieding |
| 6,221,107 B1 | 4/2001 | Steiner et al. |
| 6,231,592 B1 | 5/2001 | Bonutti et al. |
| 6,280,474 B1 | 8/2001 | Cassidy et al. |
| 6,287,324 B1 | 9/2001 | Yarnitsky et al. |
| 6,319,270 B1 | 11/2001 | Grafton et al. |
| 6,319,271 B1 | 11/2001 | Schwartz et al. |
| 6,355,053 B1 | 3/2002 | Li |
| 6,436,124 B1 | 8/2002 | Anderson et al. |
| RE37,963 E | 1/2003 | Thal |
| 6,508,830 B2 | 1/2003 | Steiner |
| 6,511,499 B2 | 1/2003 | Schmieding et al. |
| 6,517,542 B1 | 2/2003 | Papay et al. |
| 6,520,980 B1 | 2/2003 | Foerster |
| 6,524,317 B1 | 2/2003 | Ritchart et al. |
| 6,527,772 B2 | 3/2003 | Enayati |
| 6,527,794 B1 | 3/2003 | McDevitt et al. |
| 6,527,795 B1 | 3/2003 | Lizardi |
| 6,544,281 B2 | 4/2003 | ElAttrache et al. |
| 6,558,389 B2 | 5/2003 | Clark et al. |
| 6,562,044 B1 | 5/2003 | Cooper |
| 6,585,730 B1 | 7/2003 | Foerster |
| 6,610,080 B2 | 8/2003 | Morgan |
| 6,635,074 B2 | 10/2003 | Bartlett |
| 6,641,596 B1 | 11/2003 | Lizardi |
| 6,641,597 B2 | 11/2003 | Burkhart et al. |
| 6,652,561 B1 | 11/2003 | Tran |
| 6,652,563 B2 | 11/2003 | Dreyfuss |
| 6,656,183 B2 | 12/2003 | Colleran et al. |
| 6,660,008 B1 | 12/2003 | Foerster et al. |
| 6,666,877 B2 | 12/2003 | Morgan et al. |
| 6,692,516 B2 | 2/2004 | West, Jr. et al. |
| 6,699,250 B1 | 3/2004 | Osterle et al. |
| 6,716,234 B2 | 4/2004 | Grafton et al. |
| 6,773,450 B2 | 8/2004 | Leung et al. |
| 6,818,010 B2 | 11/2004 | Eichhorn et al. |
| 6,840,953 B2 | 1/2005 | Martinek |
| 6,857,520 B2 | 2/2005 | Salazar et al. |
| 6,916,333 B2 | 7/2005 | Schmieding et al. |
| 6,923,824 B2 | 8/2005 | Morgan et al. |
| 6,932,834 B2 | 8/2005 | Lizardi et al. |
| 7,037,324 B2 | 5/2006 | Martinek |
| 7,083,638 B2 | 8/2006 | Foerster |
| 7,204,839 B2 | 4/2007 | Dreyfuss et al. |
| 7,211,088 B2 | 5/2007 | Grafton et al. |
| 7,217,279 B2 | 5/2007 | Reese |
| 7,322,978 B2 | 1/2008 | West, Jr. |
| 7,329,272 B2 | 2/2008 | Burkhart et al. |
| 7,491,217 B1 | 2/2009 | Hendren et al. |
| 7,517,357 B2 | 4/2009 | Abrams et al. |
| 7,637,949 B2 | 12/2009 | Hart |
| 7,651,495 B2 | 1/2010 | McDevitt et al. |
| 7,695,495 B2 | 4/2010 | Dreyfuss |
| 7,785,347 B2 | 8/2010 | Harvie et al. |
| 7,803,173 B2 | 9/2010 | Burkhart et al. |
| 7,883,528 B2 | 2/2011 | Grafton et al. |
| 7,883,529 B2 | 2/2011 | Sinnott et al. |
| 7,887,551 B2 | 2/2011 | Bojarski et al. |
| 7,981,140 B2 | 7/2011 | Burkhart |
| 7,993,369 B2 | 8/2011 | Dreyfuss |
| 8,343,186 B2 | 1/2013 | Dreyfuss et al. |
| 2001/0002439 A1 | 5/2001 | Bonutti et al. |
| 2001/0014814 A1 | 8/2001 | Bonutti et al. |
| 2001/0018613 A1 | 8/2001 | Huene |
| 2001/0021862 A1 | 9/2001 | Bonutti et al. |
| 2002/0013608 A1 | 1/2002 | ElAttrache et al. |

(56) References Cited

U.S. PATENT DOCUMENTS

| | | | |
|---|---|---|---|
| 2002/0052629 | A1 | 5/2002 | Morgan et al. |
| 2002/0087190 | A1 | 7/2002 | Benavitz et al. |
| 2002/0111653 | A1 | 8/2002 | Foerster |
| 2002/0128684 | A1 | 9/2002 | Foerster |
| 2002/0147463 | A1* | 10/2002 | Martinek ............ 606/232 |
| 2002/0188305 | A1 | 12/2002 | Foerster et al. |
| 2003/0004545 | A1 | 1/2003 | Burkhart et al. |
| 2003/0065361 | A1* | 4/2003 | Dreyfuss ............ 606/232 |
| 2003/0069604 | A1 | 4/2003 | Schmieding et al. |
| 2003/0144696 | A1 | 7/2003 | Sinnott et al. |
| 2003/0149448 | A1 | 8/2003 | Foerster et al. |
| 2003/0191498 | A1 | 10/2003 | Foerster et al. |
| 2003/0195563 | A1 | 10/2003 | Foerster |
| 2003/0204193 | A1 | 10/2003 | Gabriel et al. |
| 2004/0030354 | A1 | 2/2004 | Leung et al. |
| 2004/0093031 | A1 | 5/2004 | Burkhart et al. |
| 2004/0106950 | A1 | 6/2004 | Grafton et al. |
| 2004/0133239 | A1 | 7/2004 | Singhatat |
| 2004/0138683 | A1 | 7/2004 | Shelton et al. |
| 2004/0138706 | A1 | 7/2004 | Abrams et al. |
| 2005/0222618 | A1 | 10/2005 | Dreyfuss et al. |
| 2005/0245932 | A1 | 11/2005 | Fanton et al. |
| 2005/0277986 | A1 | 12/2005 | Foerster et al. |
| 2005/0283156 | A1 | 12/2005 | Schmieding et al. |
| 2005/0283158 | A1 | 12/2005 | West, Jr. |
| 2006/0004364 | A1 | 1/2006 | Green et al. |
| 2006/0074434 | A1 | 4/2006 | Wenstrom, Jr. et al. |
| 2006/0079904 | A1 | 4/2006 | Thal |
| 2006/0100630 | A1 | 5/2006 | West |
| 2007/0142838 | A1 | 6/2007 | Jordan |
| 2007/0156148 | A1 | 7/2007 | Fanton et al. |
| 2007/0156149 | A1 | 7/2007 | Fanton et al. |
| 2007/0156150 | A1 | 7/2007 | Fanton et al. |
| 2007/0156176 | A1 | 7/2007 | Fanton et al. |
| 2007/0191849 | A1 | 8/2007 | ElAttrache et al. |
| 2007/0225719 | A1 | 9/2007 | Stone et al. |
| 2007/0255317 | A1 | 11/2007 | Fanton et al. |
| 2007/0260259 | A1 | 11/2007 | Fanton et al. |
| 2008/0004659 | A1 | 1/2008 | Burkhart et al. |
| 2009/0187216 | A1 | 7/2009 | Schmieding et al. |
| 2011/0015674 | A1 | 1/2011 | Howard et al. |

FOREIGN PATENT DOCUMENTS

| | | |
|---|---|---|
| EP | 1016377 | 7/2000 |
| EP | 1530951 A2 | 5/2005 |
| EP | 1762186 A3 | 3/2007 |
| EP | 1797826 B1 | 12/2009 |
| FR | 2588332 | 4/1987 |
| FR | 2622430 | 10/1987 |
| SU | 1034734 | 8/1983 |
| SU | 1600713 A1 | 10/1990 |
| WO | 99/37217 | 7/1999 |
| WO | 02/21998 A2 | 3/2002 |
| WO | 2009/055075 | 4/2009 |

OTHER PUBLICATIONS

"Bone Screw Technical Information," Richards Manufacturing Company, Inc. Tech. Publ. 1980, pp. 1-14.

"Implants for Surgery-Metal Bone Screws With Hexagonal Drive Connection, Spherical Under-Surface of Head, Asymmetrical Thread-Dimensions," International Standard ISO 5834, 1991(E), pp. 1-10.

Linvatec Revo Cancellous Screw Advertisement, 1993.

R.M. Altieri Mitek Surgical Products announces fourth-quarter and year-end results, Business Wire (Feb. 24, 1995).

Rupp et al., "Fatigue Testing of Suture Anchors," The American Journal of Sports Medicine, Mar. 2002, vol. 30, No. 2, pp. 239-247.

Laws, "Suturing Techniques," Principles of Laparoscopic Surgery, 1995, pp. 35-45.

Apreleva, Ph.D. et al., Maria, Rotator Cuff Tears: The Effect of the Reconstruction Method on Three-Dimensional Repair Site Area, Arthroscopy: The Journal of Arthroscopic and Related Surgery, vol. 18, No. 5 May-Jun. 2002: pp. 519-526.

George, MD, Michael S. et al., Suture Anchors in Arthroscopic Rotator Cuff Repair, Operative Techniques in Sports Medicine, 2004, pp. 210-214.

Millett, MD, Peter J., Mattress Double Anchor Footprint Repair: A Novel, Arthroscopic Rotator Cuff Repair Technique, Arthroscopy: The Journal of Arthroscopic and Related Surgery, vol. 20, No. 8 Oct. 2004: pp. 875-879.

Robbe, MD, Rudy et al., Knotless Suture-Based Anchors, Operative Techniques in Sports Medicine, 2004, pp. 221-224.

Thal, MD, Raymond, Knotless Suture Anchor, Arthroscopic Bankart Repair Without Tying Knots, Clinical Orthopaedics and Related Research, No. 390, 2001, pp. 42-51.

Waltrip, Robert L., Rotator Cuff Repair: A Biomechanical Comparison of Three Techniques, the American Journal of Sports Medicine, vol. 31, No. 4, 2003., pp. 493-497.

Yian, M.D., Edward et al., Arthroscopic Repair of SLAP Lesions With a Bioknotless Suture Anchor, Arthroscopy: The Journal of Arthroscopic and Related Surgery, vol. 20, No. 5, May-Jun. 2004: pp. 547-551.

Zumstein, M.D., Matthias, In Vitro Comparison of Standard and Knotless Metal Suture Anchors, Arthroscopy: The Journal of Arthroscopic and Related Surgery, vol. 20, No. 5 May-Jun. 2004: pp. 517-520.

Bacilla M.D., Phillip, "Arthroscopic Bankart Repair in a High Demand Patient Population", Arthroscopy: The Journal of Arthroscopic and Related Surgery, vol. 13, No. 1, Feb. 1997, pp. 51-60.

All Soft Tissue Anchors Are Not Created Equal . . . , Orthopaedic Biosystems Ltd., Inc., 1996.

M3-X Extremity Fixation System Just Drill and Drive, Osteomed Corporation, 1994.

Mitek GII Anchor™ System, Instrument Guide/Ordering Information, Mitek® Surgical Products, Inc., 1994.

Mitek GII Anchor™ System, Instrument Guide/Ordering Information, 1994.

Bradley M.D., James P., Labral Repair With Statak, Linvatec, 1994.

Your open techniques work . . . Let Our Arthroscopic Tools Work for You, Innovasive® Devices, Inc., 1995.

Snyder, M.D., Stephen, The Mini-Revo Labral Repair System, Linvatec, 1994.

Higgins, MD et al., Laurence D., Arthroscopic Bankart Repair, Operative Technique and Surgical Pitfalls, Clinics in Sports Medicine, vol. 19, No. 1, Jan. 2000, pp. 49-62.

Cole, MD, MBA et al., Brian J., Arthroscopic Shoulder Stabilization With Suture Anchors: Technique, Technology, and Pitfalls, Clinical Orthopaedics and Related Research, vol. 390, Sep. 2001, pp. 17-30.

Barber, M.D., F. Alan et al., Internal Fixation Strength of Suture Anchors—Update 1997, Arthroscopy: The Journal of Arthroscopic and Related Surgery, vol. 13, No. 3 Jun. 1997, pp. 355-362.

* cited by examiner

SUTURE ANCHOR

BACKGROUND

This is a continuation of U.S patent application Ser. No. 13/933,575 filed on Jul. 2, 2013, now U.S Pat. No. 8,623,052, issued on Jan. 7, 2014, which is a continuation of U.S patent application Ser. No. 12/751,266, filed on Mar. 31, 2010, which is a continuation of U.S patent application Ser. No. 11/097,172 filed on Apr. 4, 2005, now U.S Pat. No. 8,343,186, issued on Jan. 1, 2013, which claims the benefit of U.S Provisional Application No. 60/559,425, filed Apr. 6, 2004, the entire disclosure of which is incorporated by reference herein.

TECHNICAL FIELD

The present invention relates to an apparatus for anchoring surgical suture to bone. More specifically, the present invention relates to a fully threaded suture anchor provided with a transverse anchor pin for securing, within the anchor, one or more strands of suture to anchor the suture to bone during arthroscopic surgery.

When soft tissue tears away from bone, reattachment becomes necessary. Various devices, including sutures alone, screws, staples, wedges, and plugs have been used in the prior art to secure soft tissue to bone.

Recently, various types of threaded suture anchors have been developed for this purpose. Some threaded suture anchors are designed to be inserted into a pre-drilled hole. Other suture anchors are self-tapping.

U.S. Pat. No. 4,632,100 discloses a cylindrical threaded suture anchor. The suture anchor of the '100 patent includes a drill bit at a leading end for boring a hole in a bone, followed by a flight of threads spaced from the drill bit for securing the anchor into the hole created by the drill bit.

U.S. Pat. No. 5,370,662 discloses a suture anchor having threads which extend to the tip of the anchor. U.S. Pat. No. 5,156,616 discloses a similar suture anchor having an axial opening for holding a knotted piece of suture.

All of the above-noted suture anchors include structure for attaching the suture to the anchor. U.S. Pat. No. 4,632,100, for example, discloses a press-fitted disc and knot structure which secures the suture to the anchor. In other suture anchors, such as those disclosed in U.S. Pat. No. 5,370,662, the suture is passed through an eyelet located on the proximal end of the anchor. In the case of a bioabsorbable suture anchor, the suture may be insert molded into the anchor, as disclosed in U.S. Pat. No. 5,964,783.

Problems can arise if the structure for attaching the suture fails, allowing the suture to become detached from the anchor. Also, the suture often is exposed to abrasion or cutting by sharp or rough areas along the walls of the bone canal into which the anchor is inserted.

Moreover, the eyelet or, in the case of U.S. Pat. No. 4,632,100, the axial opening for receiving the disc to which the suture is knotted, is formed as part of the drive head of the known suture anchors. Combining these two functions in one structure often tends to weaken the drive head.

In addition, various other modifications to the drive head often are employed in connection with suture attachment. For example, recessed grooves may be formed on opposite sides of the drive head to receive and protect the suture from abrasive areas of the suture anchor tunnel or to facilitate mating between the anchor to the driver. In such cases, the drive head often must be made of a larger diameter to recover the mechanical strength lost from the removal of material relating to the suture-attachment or suture-protection modifications.

Further, the prior art suture anchors having eyelets extending from the proximal ends require countersinking of the eyelet below the bone surface to avoid having the patient's tissue abrade against the exposed eyelet. As a result, suture attached to the eyelet is vulnerable to abrasion by the bony rim of the countersunk hole into which the suture anchor is installed. In addition, in biodegradable suture anchors, the suture eyelet can degrade rapidly, causing the suture to become detached from the anchor prematurely.

Accordingly, there is a need for a threaded suture anchor to which suture is secured effectively so as to prevent detachment of the suture. It is further desirable for such suture anchors to have eyelets that will not abrade tissue and which do not require countersinking.

SUMMARY

An illustrative embodiment of the suture anchor of the present invention overcomes the disadvantages of the prior art discussed above by providing a threaded suture anchor having a transverse anchor pin disposed inside the body of the suture anchor. The suture anchor is made of a biocompatible metal, preferably a titanium alloy.

The proximal end surface of the threaded suture anchor of the present invention is preferably smooth and rounded to minimize suture abrasion, while the distal portion of the anchor is tapered to an elongated point to enable the anchor to be self-tapping. The proximal end portion of the suture anchor body has a hexagonally shaped opening to accept a hexagonal drive head.

The internal transverse pin provides a support over which one or more strands of suture can be looped, such that the suture is secured in a recessed fashion within the anchor.

Advantageously, suture attached to the anchor through the transverse pin exits the suture anchor through a central bore in the anchor, which prevents suture abrasion by the wall of the bone tunnel into which the anchor is inserted.

An illustrative suture anchor assembly includes an anchor body having a distal end, a proximal end, an exterior surface, a length extending along a central longitudinal axis, and a passage. The passage extends along the longitudinal axis, at least partially along the length, and from an opening at the proximal end. An external helical thread extends around the passage. The anchor body fixes a rigid member against relative movement along the longitudinal axis. The rigid member has a first dimension parallel to the central longitudinal axis and a second dimension perpendicular to the longitudinal axis, the second dimension being longer than the first dimension. The rigid member extends across the passage between a first portion of the exterior surface and a second portion of the exterior surface. A suture including ends is received about the rigid member and extends out of the opening. A driver includes a cannula having a distal opening and a proximal opening. The driver engages the anchor body, and the ends of the suture extend out of the proximal opening.

Another illustrative suture anchor assembly includes an anchor body having a distal end, a proximal end, an exterior surface, a length extending along a central longitudinal axis, and an internal passage. The passage extends along the longitudinal axis, at least partially along the length, and from an opening at the proximal end. An external helical thread extends around the passage. The anchor body fixes a rigid member against relative movement along the longitudinal axis. The rigid member has a first dimension parallel to the central longitudinal axis and a second dimension perpendicular to the longitudinal axis, the second dimension being longer than the first dimension. The second dimension of the anchor body is associated with the rigid member and is measured between a first portion of the exterior surface and a second portion of the exterior surface. A suture including ends is received about the rigid member and extends out of the opening. A driver includes a cannula having a distal opening and a proximal opening. The driver engages the anchor body, and the ends of the suture extend out of the proximal opening.

Another illustrative embodiment of a suture anchor assembly includes an anchor having a proximal end, a distal end, a longitudinal axis, a first length, and an internal passage within the anchor. The internal passage begins at an opening in the proximal end and has a second length shorter than the first length. A support structure fixed longitudinally relative to the anchor extends across the internal passage and has a third length shorter than the second length. A suture within the internal passage is received about a distal surface of the support structure. A suture extends out of the opening in the proximal end. A driver includes a cannula having a distal opening and a proximal opening, and the suture is received within the cannula. A first end and the second end of the suture extend outside of the proximal opening, the driver having a drive surface near the distal opening that engages the anchor.

Other features and advantages of the present invention will become apparent from the following description of the invention, which refers to the accompanying drawings.

DETAILED DESCRIPTION

In the following detailed description, reference is made to various specific embodiments in which the invention may be practiced. These embodiments are described with sufficient detail to enable those skilled in the art to practice the invention, and it is to be understood that other embodiments may be employed, and that structural and logical changes may be made without departing from the spirit or scope of the present invention.

Figure 1:
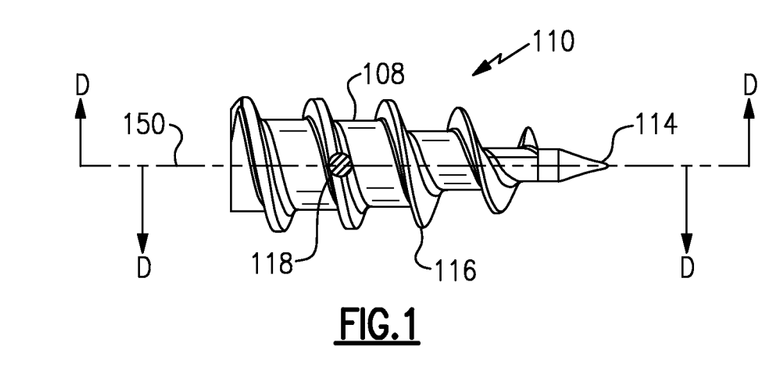
FIG. 1 is a side elevational view of the suture anchor of the present invention.

FIG. 1 illustrates a suture anchor according to a first preferred embodiment of the present invention, indicated generally by reference numeral 110. In the preferred embodiment, body 108 of anchor 110 generally tapers to a narrow point 114 at the distal end thereof. In particular, the major diameter of the anchor body is generally constant along about two-thirds of the length of the body, whereupon the diameter of the anchor then tapers to a relatively sharp point, e.g., approximately 16°. The relatively sharp distal tip of anchor 110 enables the anchor to be installed without having to first drill a hole in the bone where the anchor 110 is to be installed.

Although such tapering is preferred, suture anchor 110 may be formed to have a less tapered shape, or even cylindrical shape, to accommodate different preferences of the surgeon and/or the application of the suture anchor. For example, the tapered distal end of the anchor may be formed to be more blunt, in which case it is necessary to provide a pre-formed hole in the bone prior to insertion of the suture anchor.

A continuous thread 116 wraps around the body 108 in a clockwise direction, as shown. Anchor 110 has about five flights of thread, with the angle of the threads and other configurations of the anchor being similar to the suture anchor of U.S. Pat. No. 6,511,499, the disclosure of which is hereby incorporated by reference in its entirety.

Figure 2:
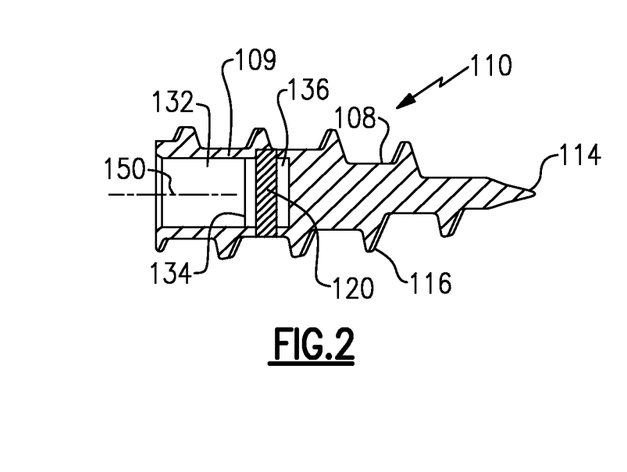
FIG. 2 is a longitudinal sectional view of the suture anchor shown in FIG. 1 through the plane D-D indicated therein.
Figure 3:
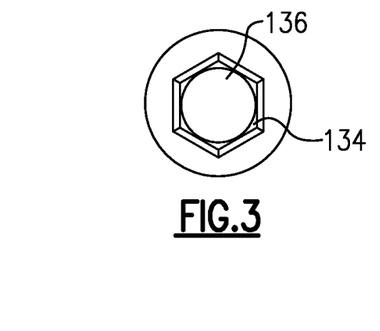
FIG. 3 is a proximal end view of the suture anchor of FIG. 1.

As can be seen more clearly with reference to FIG. 2, the proximal end portion of the anchor has a hexagonally shaped bore 132 having an opening 122 at the proximal end of anchor body 108 and extending into the anchor body approximately one-third of the length thereof. Prior art anchors have sharp edges around the drive opening, which is problematic in that sutures passing through the central opening at the proximal end of the anchor can be abraded by the sharp edges, thereby compromising the strength of the sutures. The hexagonally shaped bore 132 includes at least two internal faces (not numbered). The two internal faces intersect obliquely relative to each other. In one example, there are six internal planar faces. In the suture anchor of the present invention, the peripheral edges defining hexagonally shaped opening 122 is smooth and rounded outwardly with no sharp edges. Preferably, the opening 122 forms a slight lip curving around the diameter of the bore 132. Thus, sutures threaded through the anchor 110, as will be discussed below, will not become frayed upon being pressed or rubbed against the anchor at the proximal opening 122.

A cylindrical bore 136 having a diameter corresponding to that of the hexagonally shaped bore 132 extends from the distal end of the hexagonally shaped bore 132 to a position roughly halfway along the length of anchor body 108. The transition between hexagonally shaped bore 132 and cylindrical bore 136 forms an annular shoulder 134, against which the distal end of a hex driver 202 abuts when inserted into the hexagonally shaped bore 132 to drive the anchor into bone. A wall 109 surrounds the cylindrical bore 136 and the hexagonal shaped bore 132, as shown in FIG. 2.

Two longitudinal, diametrically opposite apertures 118 are formed in anchor body 108, the apertures 118 supporting a metal transverse anchor pin 120 which extends across cylindrical bore 136.

Figure 4:
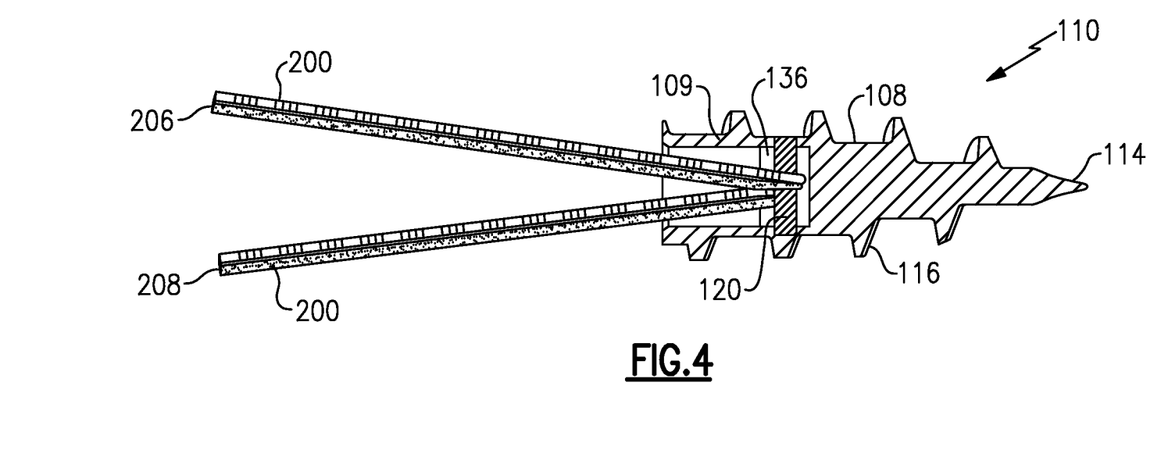
FIG. 4 is a cross sectional view of the suture anchor of FIG. 1 showing a suture looped over the transverse anchor pin.
Figure 7:
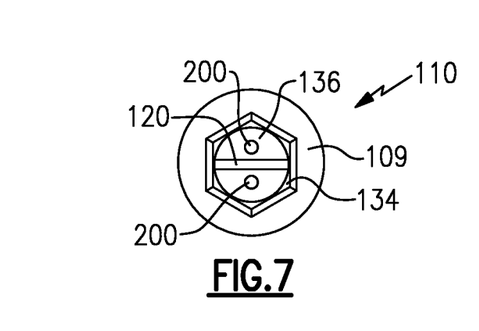
FIG. 7 is a cross section of the suture anchor of FIG. 3.

As can be seen in FIGS. 1, 2 and 4, apertures 118 extend through and interrupt the threads 116 around anchor body 108 at approximately one-third of the length of the anchor body from the distal end thereof. One or more sutures 200 are secured to the anchor by looping the suture(s) around metal anchor pin 120 as shown in FIG. 4 and FIG. 7. Although the metal anchor pin 120 is illustrated in FIGS. 2 and 4 as oriented transverse to longitudinal axis 150 of the anchor body 108, the metal anchor pin 120 may form any angle with the longitudinal axis 150 and, thus, the invention is not limited to metal anchor pin 120 forming an angle of about ninety degrees with the longitudinal axis 150 of the anchor body 108.

Preferably, suture anchor 110 is formed of a hard biocompatible metal, such as a titanium alloy, but can be made of biocompatible materials other than metal. The suture secured to the anchor may be FiberWire suture, sold by Arthrex, Inc. of Naples, Fla.

The suture anchor according to the present invention need not be formed as a threaded device, but can also be formed as a tap-in type anchor. Also, the measurements, angles and ratios between the dimensions of the suture anchor may be varied from those described above so as to be suitable for the conditions and applications in which the suture anchor is to be used.

In manufacturing the suture anchor 110 in accordance with the present invention, the anchor body 108 is cast in a die, with the bores, passageways and apertures described above either being formed during the casting process or formed afterwards. If necessary, the distal tip 114 of the anchor 110 is trimmed to the desired length and the surfaces of the anchor are polished to the desired finish.

As mentioned above, the suture anchor of the present invention may be installed in the bone without the need to pre-drill a hole in the bone. The suture anchor is installed using a driver having a shaft having a hexagonal cross-section for at least a length equal to the length of the hexagonal bore 132 from proximal opening 122 to the shoulder 134 inside the anchor 110. The driver has a cannula extending through the entire length thereof, with openings at the proximal and distal ends thereof. Of course, the outer diameter of the hexagonal shaft is sized to fit inside the hexagonal bore in the anchor so as to be enabled to drive the same.

Figure 5:
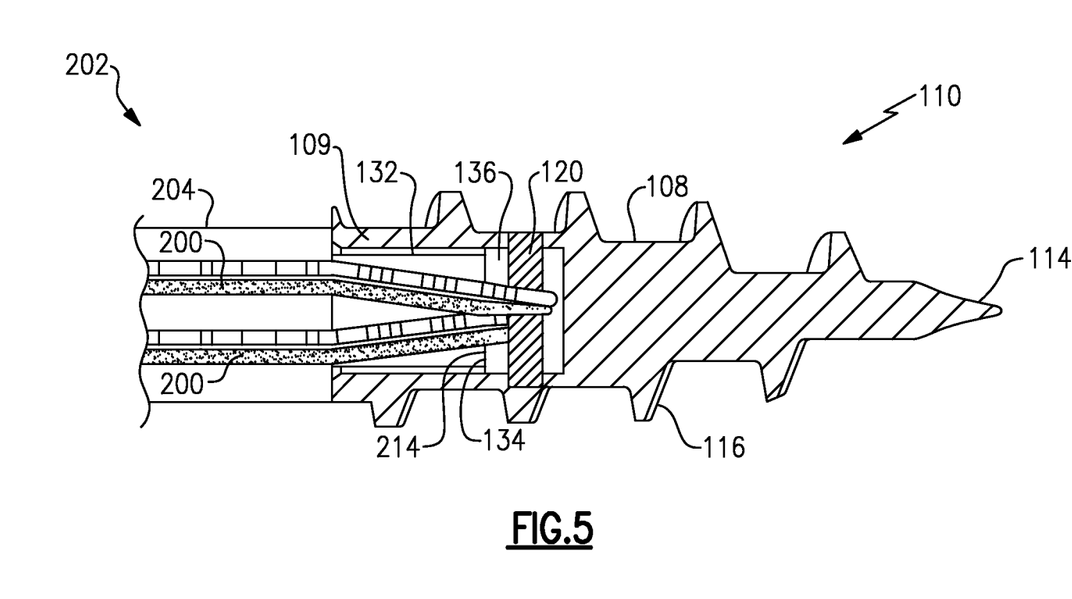
FIG. 5 is a cross sectional view of the suture anchor of FIG. 1 showing a portion of a hex driver inserted into a hexagonally shaped bore.
Figure 6:
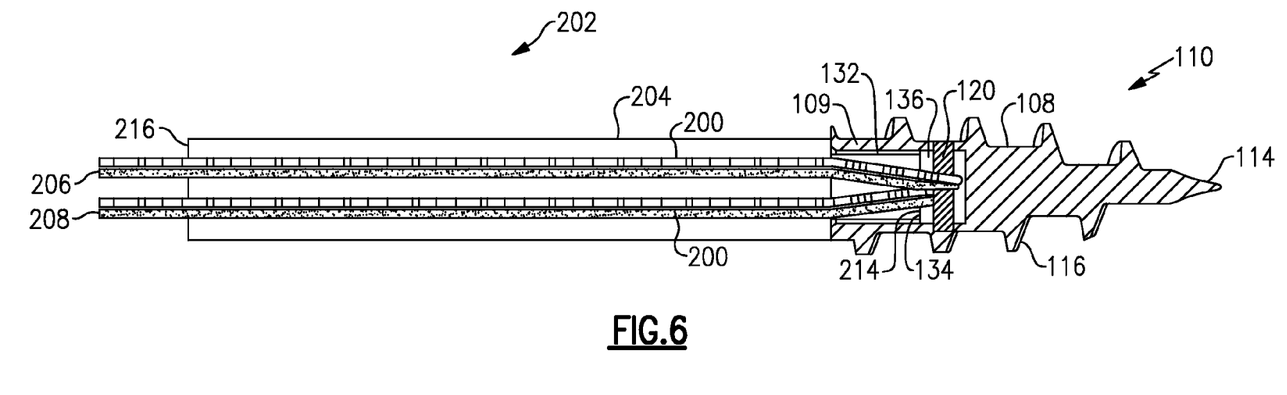
FIG. 6 is a cross sectional view of the suture anchor of FIG. 1 showing more of the hex driver inserted into a hexagonally shaped bore.

As shown in FIGS. 5 and 6, with the desired number of suture strands 200 threaded around the anchor pin 120 in the suture anchor 110, the ends 206 and 208 of the suture strands 200 are threaded through the cannula 204 in the hex driver 202 from the distal end thereof and extend from the proximal opening 216 thereof. The distal end 214 of the hex driver 202 is inserted into the proximal end of the anchor 110. With the distal end of the hex driver 202 abutting the shoulder 134 and the anchor 110 positioned at the location at which it is to be installed, the hex driver 202 is rotated to drive the anchor 110 into the bone until the proximal surface of the anchor 110 is flush with the surface of the bone.

Since it is not necessary for the proximal end of the anchor to be countersunk below the bone surface to prevent tissue abrasion by an exposed suture loop, as is required with prior art devices, the suture anchor of the present invention does not need to be inserted as far as the prior art anchors, while also avoiding abrasion of the sutures by the rim of the bone.

The suture anchor of the present invention provides greater pull-out strength of the suture loop than prior suture anchors. In addition, the suture loop of the present invention, being disposed inside the suture anchor, is protected from abrasion and degradation.

Although the present invention has been described in relation to particular embodiments thereof, many other variations and modifications and other uses will become apparent to those skilled in the art. Therefore, the present invention is to be limited not by the specific disclosure herein, but only by the appended claims.

What is claimed is:

1. A suture anchor assembly, comprising:
   an anchor body including a distal end, a proximal end, an exterior surface, a length extending along a central longitudinal axis of the anchor body, a passage, and a helical thread extending at least partially around the passage, wherein the passage extends about the central longitudinal axis, the passage extends at least partially along the length of the anchor body, and the passage extends from an opening located at the proximal end of the anchor body;
   a rigid support fixed by the anchor body against relative movement along the central longitudinal axis of the anchor body, wherein the passage is defined by a first interior surface spaced opposite to a second interior surface, and the rigid support is attached to the first interior surface and to the second interior surface, wherein the rigid support has a first dimension that is generally parallel to the central longitudinal axis of the anchor body and a second dimension that is generally perpendicular to the central longitudinal axis of the anchor body, the second dimension is longer than the first dimension, the rigid support extends across the passage and to the exterior surface, the exterior surface having a first exterior surface and a second exterior surface, the first exterior surface spaced from the second exterior surface, wherein the second dimension is defined between the first exterior surface and the second exterior surface;
   at least one tissue securing suture having a suture length and supported by the rigid support, wherein the at least one tissue securing suture includes a first end and a second end that extend out of the opening located at the proximal end of the anchor body, and the rigid support is spaced axially away from the opening at the proximal end along the central longitudinal axis; and
   a driver including a shaft having a shaft length, the shaft engaging the anchor body, and the suture length of the at least one tissue securing suture is greater than the shaft length of the shaft.

2. The suture anchor assembly of claim 1, wherein the rigid support extends through the first interior surface and the second interior surface.

3. The suture anchor assembly of claim 1, wherein the at least one tissue securing suture is received about a leading distal surface of the rigid support, the leading distal surface extending across the central longitudinal axis of the anchor body.

4. A suture anchor assembly, comprising:
   an anchor body including a distal end, a proximal end, an exterior surface, a length extending along a central longitudinal axis of the anchor body, a passage, and an external helical thread extending at least partially around the passage, wherein the passage extends about the central longitudinal axis, the passage extends at least partially along the length of the anchor body, and the passage extends from an opening located at the proximal end of the anchor body;
   a rigid support fixed by the anchor body against relative movement alone the central longitudinal axis of the anchor body;
   at least one tissue securing suture having a suture length and supported by the rigid support, wherein the at least one tissue securing suture includes a first end and a second end that extend out of the opening located at the proximal end of the anchor body, wherein the at least one tissue securing suture is received about a leading distal surface of the rigid support, the leading distal surface extending across the central longitudinal axis of the anchor body, wherein the leading distal surface extends between a first interior surface of the passage and a second interior surface of the passage spaced opposite the first interior surface, wherein at least a portion of at least one tissue securing suture is disposed in the passage between the rigid support and the opening at the proximal end; and
   a driver including a shaft having a shaft length, the shaft engaging the anchor body, and the suture length of the at least one tissue securing suture is greater than the shaft length of the shaft.

5. The suture anchor assembly of claim 4, wherein the rigid support is attached to the first interior surface and the second interior surface of the passage.

6. The suture anchor assembly of claim 4, wherein a portion of the passage is defined by a first planar passage face and a second planar passage face that are both generally parallel to the central longitudinal axis of the anchor body, the driver includes a first planar driver face and a second planar driver face, and the first planar driver face of the driver engages the first planar passage face of the passage, and the second planar driver face of the driver engages the second planar passage face of the passage.

7. A suture anchor assembly comprising:
an anchor body including a distal end, a proximal end, an exterior surface, a length extending along a central longitudinal axis of the anchor body, an internal passage, and an anchor securing contour extending at least partially around the internal passage, wherein the internal passage extends about the central longitudinal axis, the internal passage extends at least partially along the length of the anchor body, the internal passage extends from an opening located at the proximal end of the anchor body, and the internal passage is defined by a first interior surface and a second interior surface spaced opposite to the first interior surface;
a rigid support fixed by the anchor body against relative movement along the central longitudinal axis of the anchor body, wherein the rigid support is situated across the internal passage, and the rigid support branches from the first interior surface to the second interior surface;
at least one tissue securing suture having a suture length, wherein the at least one tissue securing suture includes a first end and a second end that extend out of the opening located at the proximal end of the anchor body, and at least a portion of the at least one tissue securing suture is disposed in the internal passage between the rigid support and the opening at the proximal end; and
a driver including a shaft having a shaft length, the shaft engaging the anchor body, and the suture length of the at least one tissue securing suture is greater than the shaft length of the shaft.

8. The suture anchor assembly of claim 7, wherein the anchor securing contour is an external helical thread.

9. The suture anchor assembly of claim 8, wherein the external helical thread extends around the proximal end of the anchor body.

10. The suture anchor assembly of claim 7, wherein the shaft includes a distal end and a proximal end, the shaft engaging the anchor body, and the at least one tissue securing suture extends in a direction along the central longitudinal axis of the anchor body and past the proximal end of the shaft, wherein a portion of the internal passage is defined by a first passage face and a second passage face that are both generally parallel to the central longitudinal axis of the anchor body, the driver includes a first driver face and a second driver face, and the first driver face of the driver faces the first passage face of the internal passage, and the second driver face of the driver faces the second passage face of the internal passage.

11. The suture anchor assembly of claim 7, wherein the shaft has a drive stop and the anchor body has an anchor stop, wherein the drive stop and the anchor stop abut along the central longitudinal axis of the anchor body to stop movement of the shaft into the internal passage of the anchor body.

12. The suture anchor assembly of claim 11, wherein the anchor stop is inside the anchor body.

13. The suture anchor assembly of claim 7, wherein the shaft is a cannula.

14. A suture anchor assembly, comprising:
an anchor including
a proximal end and a distal end,
a longitudinal axis,
a first length along the longitudinal axis,
an internal passage within the anchor along the longitudinal axis, the internal passage beginning at an opening in the proximal end of the anchor, the internal passage having a second length along the longitudinal axis, the second length being shorter than the first length,
a rigid suture support structure in a fixed longitudinal position relative to the anchor, the rigid suture support structure extending across the longitudinal axis, the rigid suture support structure having a third length along the longitudinal axis, the third length being shorter than the second length, wherein the rigid suture support is spaced axially away from the opening in the proximal end along the longitudinal axis, and
an anchor securing contour on at least a portion of an exterior of the anchor;
at least one tissue securing suture having a suture length and at least partially within the internal passage and supported by the rigid suture support structure with a portion of the at least one tissue securing suture being received against a leading distal surface on the rigid suture support structure, the at least one tissue securing suture including a first end and a second end, a portion of the at least one tissue securing suture extending out of the opening in the proximal end of the anchor; and
a driver including a shaft having a shaft length, the shaft engaging the anchor, and the suture length of the at least one tissue securing suture is greater than the shaft length of the shaft.

15. The suture anchor assembly of claim 14, wherein the anchor securing contour comprises a generally helical thread that is interrupted in a vicinity of the rigid suture support structure.

16. The suture anchor assembly of claim 14, wherein the anchor securing contour comprises a generally helical thread that is continuous along only some of the internal passage.

17. The suture anchor assembly of claim 14, wherein the anchor is a tap-in anchor.

18. The suture anchor assembly of claim 14, wherein
the anchor comprises a longitudinally extending wall;
the internal passage is surrounded by at least some of the longitudinally extending wall along at least a portion of the second length; and
the longitudinally extending wall is interrupted at a location corresponding to the fixed longitudinal position of the rigid suture support structure.

19. The suture anchor assembly of claim 14, wherein the anchor comprises a continuous wall along only some of the internal passage.

20. The suture anchor assembly of claim 14, wherein the rigid suture support structure is secured at the fixed longitudinal position at an interface between the rigid suture support structure and an interior surface of the internal passage.

21. The suture anchor assembly of claim 14, wherein
the rigid suture support structure has a fourth length;
the fourth length is along a direction that is generally transverse to the longitudinal axis; and
the fourth length is different than the third length.

22. The suture anchor assembly of claim 21, wherein the fourth length is greater than the third length.

23. The suture anchor assembly of claim 14, wherein the shaft engages an internal surface of the internal passage.

24. The suture anchor assembly of claim 14, wherein the rigid suture support structure comprises a generally cylindrical member at least partially received by the anchor.

25. The suture anchor assembly of claim 24, wherein the anchor includes at least one side opening in a side of the anchor and the generally cylindrical member is at least partially received through the at least one side opening.

26. The suture anchor assembly of claim 14, wherein the anchor includes at least one side opening in a side of the anchor at a position that coincides with the fixed longitudinal position of the rigid suture support structure.

27. The suture anchor assembly of claim 14, wherein the portion of the at least one tissue securing suture received against the leading distal surface on the rigid suture support structure is within a suture opening for accommodating the at least one tissue securing suture, the suture opening is disposed distal of the leading distal surface.

28. The suture anchor assembly of claim 14, wherein the at least one tissue securing suture follows a path beginning with the first end of the at least one tissue securing suture outside of the shaft, into the internal passage, around the rigid suture support structure, back through the internal passage, and ending at the second end of the at least one tissue securing suture outside of the shaft.

29. The suture anchor assembly of claim 14, wherein an entire portion of the at least one tissue securing suture that is received into the internal passage is encompassed by an exterior of the anchor.

30. The suture anchor assembly of claim 14, wherein the rigid suture support structure is secured in the fixed longitudinal position by an internal surface on the anchor.

\* \* \* \* \*

UNITED STATES PATENT AND TRADEMARK OFFICE
CERTIFICATE OF CORRECTION

| | | |
|---|---|---|
| PATENT NO. | : 8,801,755 B2 | |
| APPLICATION NO. | : 14/148460 | |
| DATED | : August 12, 2014 | |
| INVENTOR(S) | : Peter J. Dreyfuss et al. | |

It is certified that error appears in the above-identified patent and that said Letters Patent is hereby corrected as shown below:

IN THE CLAIMS:

In claim 4, column 6, line 44; delete "alone" and replace with --along--

Signed and Sealed this
Eleventh Day of November, 2014

Michelle K. Lee
*Deputy Director of the United States Patent and Trademark Office*